(12) United States Patent
Fridén

(10) Patent No.: US 7,118,581 B2
(45) Date of Patent: Oct. 10, 2006

(54) METHOD FOR FIXING A SOFT TISSUE ON A BONE

(75) Inventor: Per-Anders Fridén, Lausanne (CH)

(73) Assignee: MD Supply Sàrl, Yverdon-Les-Bains (CH)

( * ) Notice: Subject to any disclaimer, the term of this patent is extended or adjusted under 35 U.S.C. 154(b) by 576 days.

(21) Appl. No.: 10/297,066

(22) PCT Filed: May 29, 2001

(86) PCT No.: PCT/IB01/00959

§ 371 (c)(1),
(2), (4) Date: Feb. 5, 2003

(87) PCT Pub. No.: WO01/91645

PCT Pub. Date: Dec. 6, 2001

(65) Prior Publication Data

US 2003/0149449 A1   Aug. 7, 2003

(30) Foreign Application Priority Data

May 31, 2000   (CH) ..................................... 1096/00

(51) Int. Cl.
*A61F 2/38*   (2006.01)
*A61B 17/56*   (2006.01)
*A61B 17/04*   (2006.01)

(52) U.S. Cl. ......................... 606/104; 606/72; 606/232; 606/75

(58) Field of Classification Search .................. 606/72, 606/73, 75, 104, 219, 232; 227/147, 902; 411/457, 458, 460

See application file for complete search history.

(56) References Cited

U.S. PATENT DOCUMENTS

| | | | |
|---|---|---|---|
| 4,438,769 A | | 3/1984 | Pratt et al. |
| 4,793,335 A | * | 12/1988 | Frey et al. ..................... 606/73 |
| 5,012,421 A | | 4/1991 | Ishii |
| 5,224,946 A | * | 7/1993 | Hayhurst et al. ............. 606/72 |
| 5,354,292 A | | 10/1994 | Braeuer et al. |
| 5,480,403 A | * | 1/1996 | Lee et al. ...................... 606/72 |

(Continued)

FOREIGN PATENT DOCUMENTS

EP   0599772   6/1994

(Continued)

*Primary Examiner*—Julian W. Woo
(74) *Attorney, Agent, or Firm*—Davis & Bujold, P.L.L.C.

(57) ABSTRACT

The invention concerns a set for fixing a soft tissue, such as a ligament or tendon on a bone, comprising two nails (10) and a member for positioning and setting (30) the nails in the superimposed soft tissue and bone. The two nails comprise a first cylindrical upper portion and a second lower portion formed by a stepped coaxial superposition of inverted cones. The cylindrical portion is provided with a hole for passing through a suture (40) designed to constitute a way for maintaining the soft tissue in position on the bone during healing. The positioning and setting member (3) comprises a handle (31) wherein is nested a cylindrical rod (32) including an end (33). The U-shaped end comprises two branches (35) provided with a blind cylindrical bore designed to receive the cylindrical part of the nails (10). When the nails are secured to the member (30), the suture (40) is maintained by the stop elements (34) of the handle (31).

10 Claims, 3 Drawing Sheets

U.S. PATENT DOCUMENTS

| | | |
|---|---|---|
| 6,149,669 A | 11/2000 | Li |
| 6,179,840 B1 * | 1/2001 | Bowman ................... 606/72 |
| 6,187,009 B1 | 2/2001 | Herzog et al. |
| 6,190,401 B1 | 2/2001 | Green et al. |
| 6,554,852 B1 * | 4/2003 | Oberlander ................ 606/232 |

FOREIGN PATENT DOCUMENTS

| | | |
|---|---|---|
| EP | 0770354 | 5/1997 |
| EP | 0835640 | 4/1998 |
| EP | 0916311 | 5/1999 |
| EP | 1070487 | 1/2001 |

* cited by examiner

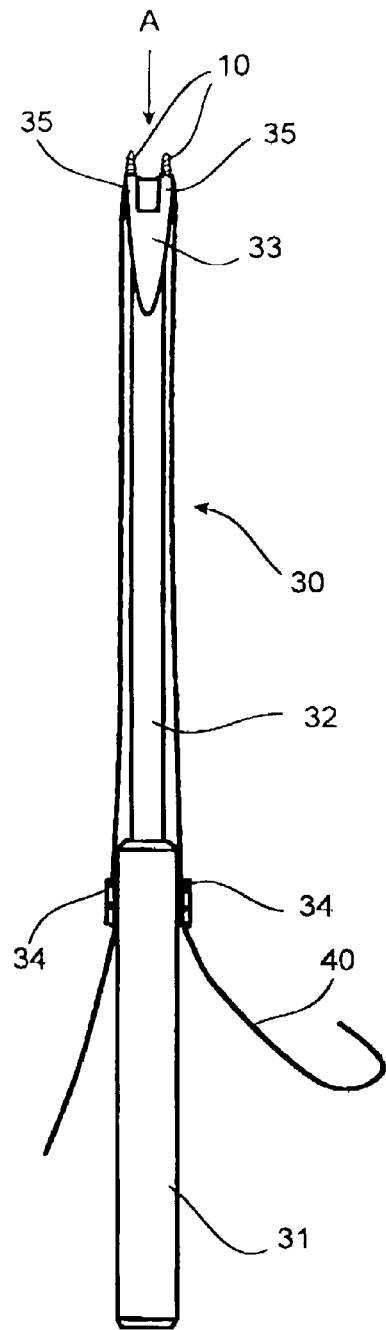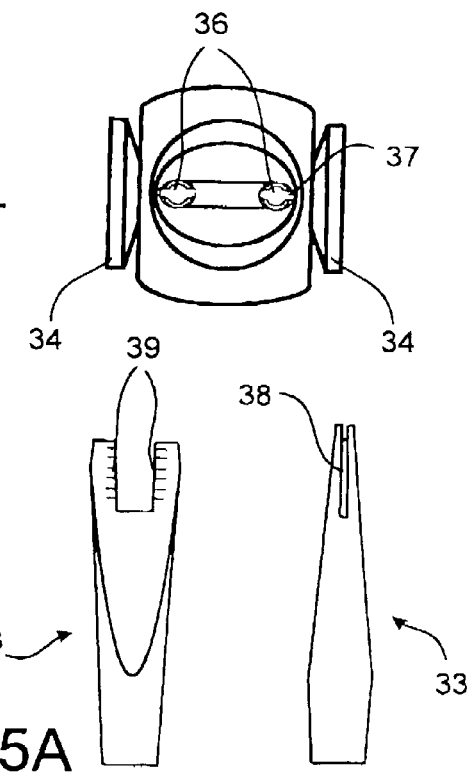
FIG. 3
FIG. 4
FIG. 5A
FIG. 5B

METHOD FOR FIXING A SOFT TISSUE ON A BONE

TECHNICAL DOMAIN

This invention relates to a system of fixing connective tissue, notably a ligament or tendon, to a bone by means of at least two pins, each pin comprising an upper cylindrical section and a lower section made up of superposed inverted cones with a directrix whose diameter is greater than the diameter of the cylindrical section, the fixing system including a means of connecting the two pins, some means for holding the connective tissue in position on the bone once the pins have been put in place, each pin formed so as to prevent its vertical movement in the bone after it is put in place.

It relates, as well, to a procedure for fixing connective tissue, notably a ligament or a tendon, to a bone by means of at least two pins, by means of the fixing system according to the invention.

PRIOR ART

Ligamentous lesions are more common after multiple accidents, notably occurring in the field of sport. A ligament reconstruction is then necessary and this needs to be durable.

In most current orthopaedic surgery, the fixing of a ligament or tendon, which has been torn at the bone ridge, is done using the type of staples commonly used nowadays in surgery. However, when these staples are used, there is always a metal part which protrudes from the surface of the connective tissue and which could cause tissue necrosis.

This type of fixation can also be done using appropriate screws. One of the major disadvantages of these screws is that the bone must be pierced in order to insert them. Another disadvantage is that the exact positioning spot is difficult to determine.

An initial form of one of the well-known fixing elements is described in the European publication EP 0 770 354 which has as its object a device which behaves like a stapler but which resembles a gun fitted with a longitudinal housing forming a magazine in which all the fixing elements are stored one inside the other. This mechanism is aimed exclusively at the repair of tissue torn in the meniscus of the knee, the staples are lactic acid-based, are reabsorbable and cannot be implanted in the bone. Furthermore, by its design, the spacing between the two fixing elements is necessarily unchangeable, which makes the invention unusable for a large variety of applications. As mentioned previously, the existence of a semi-rigid connection between the two fixing elements can cause tissue necrosis. Finally, it is only possible to connect the two fixing elements two at a time and it is not possible to connect three or four elements, which could be necessary when there is a large attaching surface.

Another form of manufacturing a fixing element is described in the patent U.S. Pat. No. 5,012,421. This document relates to a pin, which allows the anchoring of a suture material extremity in a bone. This pin consists of a superior cylindrical section in which the suture material extremity is imprisoned and an inferior section formed by a superimposition of inverse cones. The pin is put in place with a tool comprising at its extremity, which is in contact with the bone, a cylindrical blind cavity designed to receive the cylindrical part of the pin. This type of element has the notable disadvantage that, because of its size, it destroys tissue when it is inserted. It can therefore not be introduced through the tissue but must be placed next to the tissue. Inserting it is therefore difficult. Moreover, the pin has spiral grooves, which make it turn on itself when it is inserted in the bone. This prevents the use of the bone's 'elasticity', which makes the bone stretch to allow the pin to penetrate when it is driven into the bone, and then take up its initial position to maintain the pin firmly. The fact that the suture material is joined to the pin means that it is not possible to use suture material with which users are used to working. In addition, when the suture material is used to fix connective tissue, there is only one bridge between the two pins. So, many operations fail due to rupture of the tissue by the suture material which must be, on the one hand, sufficiently taught to hold the tissue; and, on the other hand, sufficiently flexible not to cut it.

The publication EP 0 835 640 describes an anchoring device inside a bony substance, for suture material fitted with a needle at each of its extremities. To avoid prior piercing of the bone, the supporting element receiving the suture material and which is to be anchored in the bony substance has a pointed extremity area serving as an injector needle, a threaded tapered area to ensure the self-threading function and a cylindrical area to ensure anchoring in the bone. The element's inserting device is in the form of a screw driver, the support element being introduced into the bone by self-threading, formed by a shaft and a stem whose free extremity is designed to work together with the superior part of the support element. The shaft of this device consists of a recess to house the needle-thread system and the stem is fitted with a longitudinal slit to receive the two strands of thread when the support element is put in place. This device, like the previous one, does not allow two anchorages to be done in one step, and there is no parallelism between two elements inserted one after the other. The loss of parallelism means it can be pulled out easily.

Prior art techniques allow either for two fixing elements to be introduced at the same time, with a spacing which cannot be modified, or for a single element to be introduced at one time, that turns during its introduction. Moreover, they produce a compression not adapted to the tissue surface, which could cause either necrosis or rupture in the tissue.

PRESENTATION OF THE INVENTION

This invention aims to alleviate the disadvantages of previous techniques by offering a system allowing for precise and rapid fixing of connective tissue to bone, without an apparent metallic element and without piercing the bone. This system offers a large contact and scarring surface between the tissue and the bone, without risk of tissue necrosis, and ensures reliable fixation with no risk of the pins being pulled out due to an approximate implementation. Moreover, the risk of cutting off the tissue by the suture material is practically non-existent.

To that end, this system, as described in the preamble, is characterised in that it consists of a device for simultaneously positioning and inserting, in the superposed connective tissue and bone, two pins joined by a connecting means, with a defined spacing between them, and in that the connecting means is suture material.

The cylindrical section consists, preferably, of a cylindrical transversal bore designed to work together with the connecting means.

The device for positioning and inserting comprises, advantageously, a shaft in which a cylindrical stem is inserted, fitted with one fork-shaped extremity having two branches whose distance between the longitudinal axes is equal to the said defined distance between the longitudinal axes of the pins.

Each branch of the fork can contain a blind cylindrical bore designed to work together with the cylindrical section of a pin and two lateral notches designed to receive the suture material.

In a preferred manufacturing form, the shaft comprises two stopping elements diametrically opposite and designed to retain the suture material when the pins, connected by the said suture material, are integral with the extremity so as to be trained onto the connective tissue situated above the bone.

In a preferred manufacturing form, the extremity of the fork comprises a means to control the depth at which the pins are inserted into the bone.

Advantageously, the system according to the invention can contain a prepositioning element for the spacing between two pins. This spacing prepositioning element consists of, preferably, two housings designed to receive the inferior section of the pins, the longitudinal axes of these housings being spaced at a distance equal to the defined spacing of the longitudinal axes of the said pins. It can equally consist of a means of maintaining the pins in the said housings in a defined position.

The aims of the invention are equally achieved by a procedure such as defined in the preamble and characterised in that it consists of the steps comprising joining two pins with the aid of a connecting means, grasping the two pins, using a device trained at the tissue to be fixed for positioning and inserting simultaneously in the superposed connective tissue and bone the two pins, by controlling the depth of their insertion, and ensuring the connective tissue is put in place on the bone with the maintaining means.

SUMMARY DESCRIPTION OF THE DRAWINGS

The present invention will be better understood by referring to the description of a preferred and non limiting form of manufacture and to the attached drawings in which:

FIG. 3 illustrates the positioning and inserting device of the two pins, as well as the means for connecting the two pins;

FIG. 4 is an enlarged view along Arrow A in FIG. 3 of the positioning and inserting device;

FIGS. 5A and 5B are enlarged representations of, respectively, the opposite and lateral extremities of prehension of the pins of the positioning and inserting device in FIG. 3

THE BEST IMPLEMENTATION OF THE INVENTION

Referring to the figures, the fixing system according to the invention consists of two pins 10 for attaching a connective tissue, such as the extremity of a tendon or ligament, to a bone ridge during reparative surgery. In order to facilitate the imposition of the two pins by inserting them in the bone simultaneously with a defined space between them, as when using staples, the fixing system as illustrated by the figures has, as well, a pro-positioning element 20 for the pins 10, as well as a device to position and insert (positioning and position maintaining mechanism) 30 the pins in the superposed connective tissue and bone. When they have been put in place, the two pins are connected by a connecting means 40 made up of suture material for creating the means of maintaining in position 50 the connective tissue on the bone.

Figure 1:
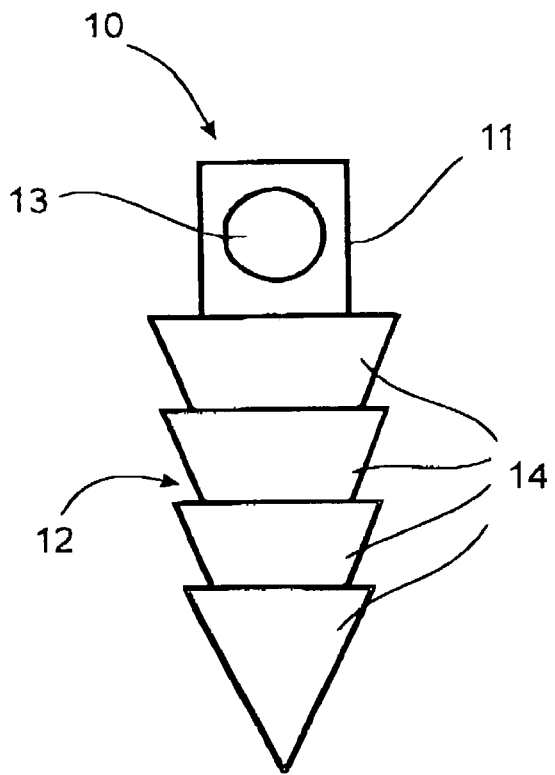
FIG. 1 is an elevated view of one of the pins used in the fixing system according to the invention

The pins 10 as illustrated by FIG. 1, and whose conical 'pine tree' shape has been specially designed to obtain a solid fixation, comprises a first superior cylindrical section 11 and a second inferior section 12 formed by a co-axial 'staircase' superimposition of inverted cones 14. The cylindrical section 11 is fitted with a cylindrical chamfered bore 13, laid out transversally and whose function will be detailed later. The cones 14 of the inferior section 12 are formed by a generator which creates an angle of approximately 60° relative to the vertical median axis of the pin and whose directrix diameter is superior to the diameter of the cylindrical portion 11. In order to facilitate the perforation of the connective tissue, the generator of the cone 14 forming the extremity of the pin forms an angle of approximately 50° relative to the vertical axis.

Figure 2:
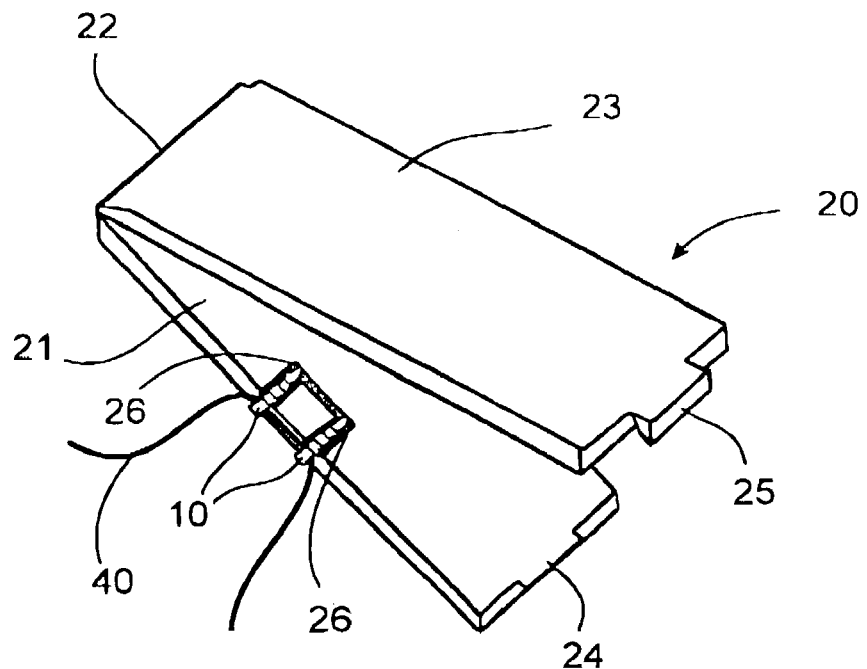
FIG. 2 represents a perspective view of a pin prepositioning element

The prepositioning element 20 of the two pins 10, as illustrated by the FIG. 2, and whose use is not obligatory in the invention procedure, is in the form of a squeezing device comprising one inferior part 21 connected by a joint 22, to a superior part 23. The two parts 21 and 23 are rectangular parallelepipeds and comprise respectively a flat inferior and superior face, which can be pressed against each other. The element 20, is further fitted with a means of closing to keep the two faces in contact. To that end, the inferior part 21 is fitted with a jutting edge 24 on its lateral face opposite the joint 22, which works together with a corresponding edge 25, in the shape of a hook, arranged on the superior part 23. The inferior part 21 is further fitted with two housings for receiving the two pins 10. These housings are positioned next to one another and their longitudinal axes are spaced at a distance equal to the defined spacing of the two pins' longitudinal axes when these are inserted in the bone. The depth and the width of these housings 26 are, respectively, equal to the diameter of the directrix of the cones 14 and their length is equal to the length of the inferior section 12 of the pins 10. Thus, when the device is closed again after the pins are inserted in the housings 26, the bores 13 being placed in each other's extension, only the cylindrical parts 11 protrude from the element 20, The two pins 10 are therefore connected by the connecting means 40 which is made to pass through each bore 13.

In order to ensure the introduction of the pins 10 thus positioned and fitted with the suture material 40 over the connective tissue situated on the bone, the positioning and inserting device 30 is used, as illustrated by FIGS. 3 to 5.

This device 30, as represented by FIG. 3, has a shaft 31 which can have an approximately squared (as illustrated) or cylindrical section, preferably manufactured in rustproof steel, and in which a cylindrical stem 32 is inserted, preferably in rustproof steel, comprising one extremity 33 which is ovoid in shape and which will be described with reference to FIGS. 4 and 5. This shaft 31 is further provided with two conical stopping elements which are diametrically opposite on each of its faces. Their function will be detailed later.

The extremity 33 of the stem 32, represented in more detail by FIGS. 4, 5A and 5B, has a fork-like shape in a U comprising two branches 35 whose distance between the longitudinal axes is equal to the defined space of the pins' longitudinal axes. Each branch 35 is provided with a cylindrical blind bore whose diameter is approximately superior to that of the cylindrical part 11 of the pins and whose depth is at least equal to the height of this part 11. A median transversal slit 37 is situated across these bores 36. This slit 37 extends from each side of each branch 35 with two vertical grooves 38, which, preferably, curve inwards and are illustrated by the FIG. 5B. The interior edges of the branches 35 forming the sides of the U are fitted with a graduation in millimeters forming the controlling means 39 for the depth of insertion of the pins in the bone, as illustrated by the FIG. 5A.

Figure 6:
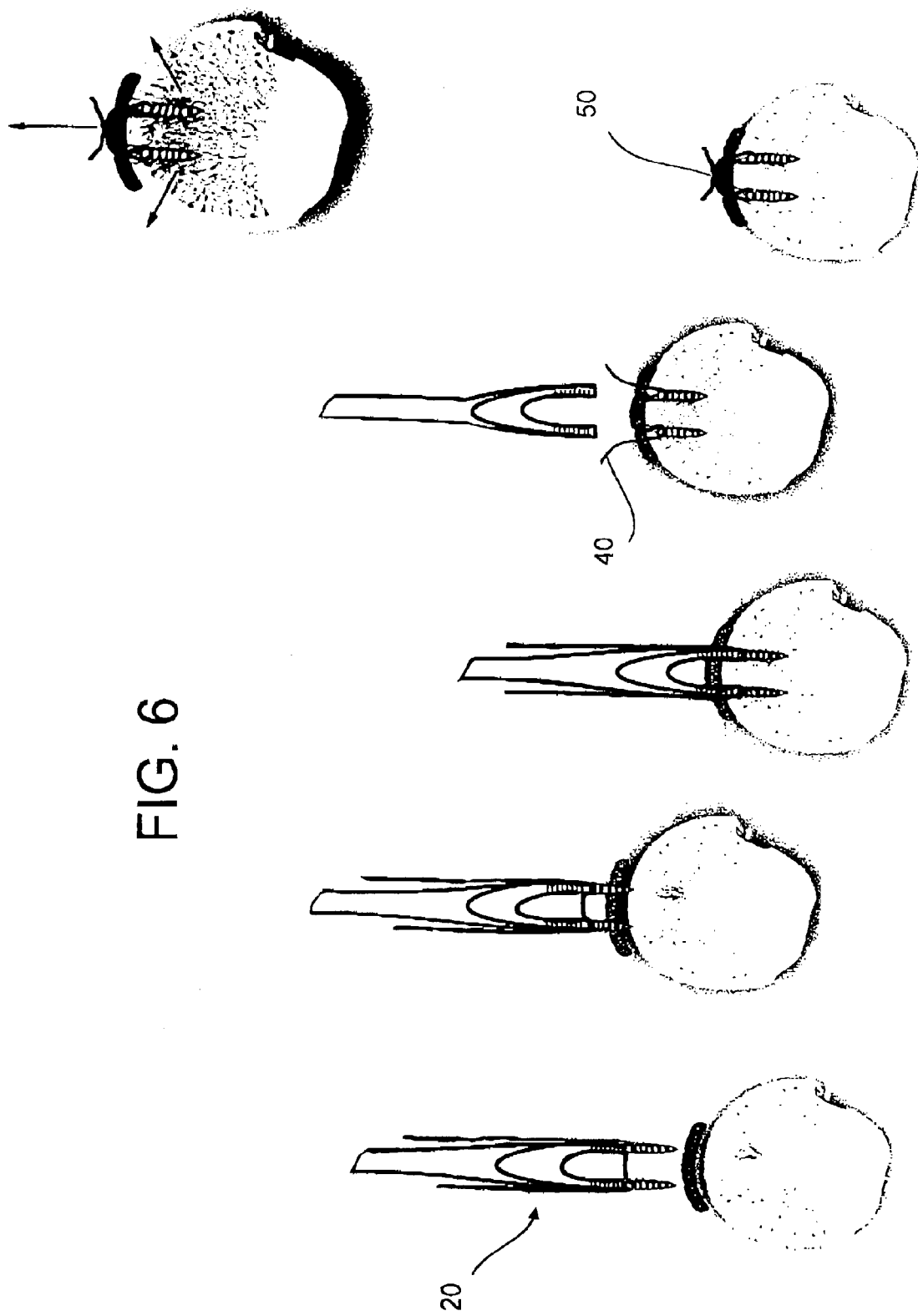
FIG. 6 shows, respectively, the various steps of the procedure according to the invention.

The various steps for using the system according to the invention, as illustrated by the FIG. 6, occur in the following way:

When using the prepositioning element 20, this element being open, the portion 12 of the pins 10 are placed in the housings 26 previewed for this purpose, the cylindrical portion 11 protruding over the edge of the inferior part 21. The element 20 is shut again, the hook-shaped edge 25 hanging from the jutting edge 24, so as to immobilise the pins in their housing. The bores 13 of the cylindrical section 11 of the pins having been arranged in each other's extension during this insertion, they are connected by threading the suture material 40 in the two bores 13.

The pins 10 and the thread 40 in place, the positioning and inserting device 30 is taken by the shaft 31 and the extremity 33 is applied to the pins, the cylindrical part 11 entering the blind bores 36 of the two branches 35, the suture material 40 lodging itself in the slit 37. So that the pins do not separate from the extremity 33 when opening the element 20, the free extremities of the suture material 33 are wound around the stopping elements 34 arranged on the shaft, allowing the suture material to pass in the exterior lateral grooves 38.

The connective tissue to be fixed having been positioned over the bone ridge, the tissue is directed to the place where it must be resoldered to the bone and the extremity of the pins are positioned at this point by taking the device 30 and the pins 10 along the normal line of the bone surface. The pins can then be inserted by hitting on them with an appropriate hammer on the free extremity of the shaft 31. The depth of the insertion is controlled with a graduation of the extremity 33 means of control. The U shape of this extremity 33 ensures the connective tissue is not damaged between the two pins 10 since it has just been housed between the two branches 35, the suture material 40 which joins them maintaining the tissue in place during this operation. The grooves 38 further protect the suture material 40 during this insertion.

When the pins 10 are inserted, they are separated from the device 30 by freeing the suture material 40 whose two extremities form a knot 51, which constitutes the maintaining in position means 50 of the connective tissue on the bone. This double join by the suture material means there is no risk of cutting the tissue.

Because of its design, this mode of fixing is reliable. This is because in one way the individual 'pine tree' shape of the pins allows the bone to be compressed and as a consequence a biological self-blocking reaction of the pin. In another way, the pins being joined by suture material, any tension exerted on the material tends to modify the parallelism of the pins whose points reach towards the exterior, which reinforces the solidity of the fixing.

It should be further noted that this system ensures the parallelism of the pins during their insertion and guarantees that no metallic part protrudes from the bone surface during the operation. When the two pins are not in the same plane, there is more risk of being pulled out. Because of its design, this type of fixing can be used in endoscopy as well as in open surgery.

The use of these pins also means that any kind of suture material may be used. It is also possible, during operations on a large surface, to use four or more pins and to join all these pins. This allows optimal fixing of the tissue to the bone.

When there is increased risk of cutting the tissue, it is possible to pass the suture material several times through the pins, which increases the maintaining surface of the tissue and diminishes the risk of rupturing.

Thus, thanks to the use of the pins and the system according to the invention, the intervention is simplified and quicker since it is possible to hold the connective tissue with the pins' extremities, to fix them by inserting the pins and knotting the suture material very quickly; all the while adapting it to a great variety of different operations.

The invention claimed is:

1. A fixing system for fixing connective tissue to a bone, the fixing system comprising at least two pins, each of the at least two pins comprising a superior section and an inferior section, the superior section having an opening for passage of a suture thread therethrough for interconnecting the at least two pins with one another, the inferior section comprising a plurality of superimposed inverted cones, the superior section forming a cylindrical tip, the opening for passage of the suture thread being a transverse cylindrical bore which, during use, cooperates with the suture thread, and the fixing system further comprising a positioning and position maintaining mechanism for simultaneously positioning and maintaining the connective tissue superimposed over the bone, the positioning and position maintaining mechanism comprising a shaft having a cylindrical stem, the cylindrical stem having a fork-like end part with two branches, and a spacing between longitudinal axes of the two branches being equal to a spacing of the at least two pins from one another; and each of the two branches is provided with a cylindrical bore for cooperating with the cylindrical tip of the superior section of one of the at least two pins and with two lateral grooves for receiving the suture thread.

2. The fixing system according to claim 1, wherein the shaft has two diametrically opposite stopping elements for holding the suture thread when the at least two pins, interconnected by the suture thread, are attached to the end part of the positioning and position maintaining mechanism while the positioning and position maintaining mechanism, the suture thread and the at least two pins are manipulated relative to the connective tissue superimposed over the bone.

3. The fixing system according to claim 1, wherein the end part of the cylindrical stem of the positioning and position maintaining mechanism comprises a control mechanism for controlling an insertion depth of the at least two pins into the bone.

4. The fixing system according to claim 1, wherein the fixing system further comprises a prepositioning element for spacing the at least two pins from one another before the at least two pins are grasped by the positioning and position maintaining mechanism.

5. The fixing system according to claim 4, wherein the prepositioning element comprises two housings for receiving the inferior section of each of the at least two pins, and longitudinal axes of the two housings are spaced from one another by a distance equal to the spacing of the longitudinal axes of the at least two pins from one another, and the prepositioning element comprises a mechanism for maintaining the at least two pins in a predetermined position within the two housings.

6. The fixing system according to claim 1, wherein the connective tissue is one of a ligament and a tendon.

7. A fixing system for fixing connective tissue to a bone, the fixing system comprising at least two pins, each of the at least two pins comprising a superior section and an inferior section, the superior section having an opening for passage of a suture thread therethrough for interconnecting the at least two pins with one another, the inferior section comprising at least one inverted cone, the superior section forming a tip, the opening for passage of the suture thread being a bore which, during use cooperates with the suture thread, and the fixing system further comprising a positioning and position maintaining mechanism for simultaneously positioning and maintaining the connective tissue superimposed over the bone, the positioning and position maintaining mechanism comprising a shaft having a stem, the stem having an end part with two branches, and a spacing between the two branches being equal to a spacing of the at least two pins from one another; and each of the two branches is provided with a bore for cooperating with the tip of the superior section of one of the at least two pins and with two lateral grooves for accommodating the suture thread.

8. The fixing system according to claim 7, wherein the connective tissue is one of a ligament and a tendon.

9. A procedure for fixing connective tissue to a bone by at least two pins, each of the at least two pins comprising a superior section and an inferior section, the superior section having an opening for passage of a suture thread therethrough for interconnecting the at least two pins with one another, the inferior section comprising a plurality of superimposed inverted cones; wherein the superior section has a cylindrical tip, the opening for passage of the suture thread permitting passage of at least one pass of the suture thread, and the fixing system further comprises a positioning and position maintaining mechanism for simultaneously positioning and maintaining the connective tissue superimposed over the bone, the positioning and position maintaining mechanism comprising a forked end part with two branches, and a predetermined distance between the two branches defines a spacing of the at least two pins from one another, in which the procedure comprises the steps of:

joining the at least two pins with one another by the suture thread;

grasping two of the at least two pins by the positioning and position maintaining mechanism and placing the two pins over the connective tissue to be fixed to the bone;

simultaneously inserting the two pins in the connective tissue superimposed over the bone and controlling an insertion depth of the two pins into the bone; and retaining positioning of the connective tissue relative to the bone by a maintaining mechanism formed by knotting two extremities of the suture thread.

10. The procedure according to claim 9, wherein the connective tissue is one of a ligament and a tendon.

* * * * *